(12) United States Patent
Kawamata et al.

(10) Patent No.: US 7,893,018 B2
(45) Date of Patent: Feb. 22, 2011

(54) METHOD OF TREATMENT FOR ISCHEMIC HEART DISEASE

(75) Inventors: Shin Kawamata, Kobe (JP); Yoshiki Sawa, Suita (JP); Satoru Sakakida, Suita (JP); Shinya Fukui, Suita (JP); Yoshinobu Murakami, Kobe (JP); Hirokazu Hirata, Kobe (JP)

(73) Assignee: Foundation for Biomedical Research and Innovation, Kobe-shi (JP)

( * ) Notice: Subject to any disclaimer, the term of this patent is extended or adjusted under 35 U.S.C. 154(b) by 135 days.

(21) Appl. No.: 12/084,547

(22) PCT Filed: Nov. 8, 2006

(86) PCT No.: PCT/JP2006/322782

§ 371 (c)(1),
(2), (4) Date: May 5, 2008

(87) PCT Pub. No.: WO2007/055397

PCT Pub. Date: May 18, 2007

(65) Prior Publication Data

US 2009/0270313 A1    Oct. 29, 2009

Related U.S. Application Data

(60) Provisional application No. 60/734,285, filed on Nov. 8, 2005.

(51) Int. Cl.
*A61K 38/00*   (2006.01)
*A61K 38/16*   (2006.01)
*A61K 38/17*   (2006.01)

(52) U.S. Cl. ..................... 514/1.1; 514/16.4; 514/21.2

(58) Field of Classification Search ...................... None
See application file for complete search history.

(56) References Cited

U.S. PATENT DOCUMENTS

| | | | | |
|---|---|---|---|---|
| 7,294,334 | B1 * | 11/2007 | Michal et al. | 424/93.7 |
| 7,638,128 | B2 * | 12/2009 | Dzau et al. | 424/185.1 |
| 2004/0219129 | A1 * | 11/2004 | Yoshida et al. | 424/85.1 |
| 2005/0079151 | A1 | 4/2005 | Ikematsu et al. | |

FOREIGN PATENT DOCUMENTS

| | | |
|---|---|---|
| CN | 1579539 | 2/2005 |
| JP | 08-027021 | 1/1996 |
| JP | 2004-503602 | 2/2004 |
| JP | 2004-115413 | 4/2004 |
| JP | 2005-068122 | 3/2005 |
| JP | 2005-506279 | 3/2005 |
| WO | WO-98/35043 A1 | 8/1998 |
| WO | WO-02/05857 A2 | 1/2002 |
| WO | WO-02/46225 A2 | 6/2002 |
| WO | WO-2004-113513 A2 | 12/2004 |

OTHER PUBLICATIONS

Horiba, M. et al., "Midkine plays a protective role against cardiac ischemia/reperfusion injury through a reduction of apoptotic reaction," Circulation, 2004, vol. 110, No. 17, Suppl. S, p. 106.
Christman, K. L. "Pleiotrophin induces formation of functional neovasculature in vivo," Biochemical and Biophysical Research Communications, Jul. 2005, vol. 332, No. 4, p. 1146-1152.
Philp, D. et al., "The action binding site on thymosin β-4 promotes angiogenesis," The FASEB Journal, 2003, vol. 17, No. 14, p. 2103-2105.
Bock-Marquette, I. et al., "Thymosin β 4 activates integrin-linked kinase and promotes cardiac cell migration, survival and cardiac repair," Nature, 2004, vol. 432, No. 7016, p. 466-472.
Barandon, L. et al., "Reduction of infarct size and prevention of cardiac rupture in transgenic mice overexpressing FrzA," Circulation, 2003, vol. 108, No. 18, p. 2282-2289.
Rattner, A. et al., "A family of secreted proteins contains homology to the cysteine-rich ligand-binding domain of frizzled receptors," Proceedings of the National Academy of Sciences of the United States of America, 1997, vol. 94, No. 7, p. 2859-2863.
Sumida, A. et al., "Midkine prevents the cardiac remodeling in mice after myocardial infarction and improves their long-term survival," Circulation Journal, Mar. 2006, vol. 70, No. Suppl.1, p. 274.
Horiba, M. et al., "Midkine plays a protective role against cardiac ischemia/reperfusion injury through a reduction of apoptotic reaction," Circulation, Oct. 2006, vol. 114, No. 16, p. 1713-1720.
Letters to Nature, Nature, vol. 428, Apr. 2004, p. 668-673.
Sherwood, R. I. et al., "Isolation of Adult Mouse Myogenic Progenitors: Functional heterogeneity of Cells within and Engrafting Skeletal Muscle," Cell, vol. 119, Issue 4, Nov. 12, 2004, pp. 543-554.
Tam SK et al., "Molecular cardiomyoplasty" potential cardiac gene therapy for chronic heart failure, J. Thorac and Cardiovasc Surgery, May 1995, 918-924 (1 sheet).
He, B. et al., "Secreted Frizzled-Related Protein 4 is Silenced by Hypermethylation and Induces Apoptosis in β-Catenin-Deficient Human Mesothelioma Cells," Cancer Res. 65 (3), Feb. 1, 2005, p. 743-748.
Lee, J-L. et al., "Autocrine/Paracrine Secreted Frizzled-related Protein 2 Induces Cellular Resistance to Apoptosis," J. Biol. Chem. 279 (15), 2004, 14602-14609.
Owada, K. et al., "Midkine inhibits apoptosis via extracellular signal regulated kinase (ERK) activation in PC12 cells," J Med Dent Sci. 46(1), 1999, 45-51 (1 sheet).
Bowden, E. "Anti-apoptotic signaling of pleiotrophin through its receptor, anaplastic lymphoma kinase," J Biol Chem. 277(39), 2002, p. 35862-35868.

(Continued)

*Primary Examiner*—Elizabeth C. Kemmerer
(74) *Attorney, Agent, or Firm*—Edwards Angell Palmer & Dodge LLP

(57) ABSTRACT

The present invention provides a method of treatment for ischemic heart disease administering a scar formation accelerator containing at least one selected from SFRP2, SFRP4, Midkine, Pleiotrophin and Thymosin beta-10 as an effective ingredient to promote scar formation less fibrosis and retaining elasticity, and thereby improving cardiac function.

7 Claims, 8 Drawing Sheets

OTHER PUBLICATIONS

Rho, S. B. et al., "The identification of apoptosis-related residues in human thymosin β-10 by mutational analysis and computational modeling," J. Biol. Chem. 280 (40), 2005, p. 34003-34007.

Kadomatsu, K. et al., "Midkine and pleiotrophin in neural development and cancer," Cancer Letter. Feb. 20, 2004; 204: 127-143 (1 sheet).

Mitsiadis, T. A.et al., "Expression of the heparin-binding cytokines, midkine (MK) and HB-GAM (pleiotrophin) is associated with epithelial-mesenchymal interactions during fetal development and organogenesis," Development, 121, 1995; p. 37-51.

Takada, J. et al., "Postischemic gene transfer of midkine, a neurotrophic factor, protects against focal brain ischemia," Gene Therapy. 2005;12:p. 487-493.

Ochiai K. et al., "The role of midkine and pleiotrophin in liver regeneration," Liver Int. 2004;24: 484-491 (1 sheets).

Obama, H. et al., "Myocardial infarction induces expression of midkine, a heparin-binding growth factor with reparative activity," Anticancer Res. 1998; 18: 145-152 (1 sheet).

Sato, W. et al., "Midkine is involved in neutrophil infiltration into the tubulointeristitium in ischemic renal injury," J. Immunol. 2001;167:p. 3463-3469.

International Search Report mailed on Jan. 16, 2007, issued on the PCT International Application No. PCT/JP2006/322782.

Heike Schumann et al., "Expression of secreted frizzled related proteins 3 and 4 in human ventricular myocardium correlates with apoptosis related gene expression," Cardiovascular Research, vol. 45, 2000, pp. 720-728.

Jonathan M. Levin, "SFRP2 expression in rabbit myogenic progenitor cells and in adult skeletal muscles," Journal of Muscle Research and Cell Motility, vol. 22, 2001, pp. 361-369.

Supplementary European Search Report dated Jun. 10, 2010, issued in the European Patent Application No. 06823430.1.

* cited by examiner

SEQUENCE LISTING

<160> NUMBER OF SEQ ID NOS: 6

<210> SEQ ID NO 1
<211> LENGTH: 18
<212> TYPE: DNA
<213> ORGANISM: Artificial sequence
<220> FEATURE:
<223> OTHER INFORMATION: MDK primer1

<400> SEQUENCE: 1
cggatggtct cctggcac                                            18

<210> SEQ ID NO 2
<211> LENGTH: 18
<212> TYPE: DNA
<213> ORGANISM: Artificial sequence
<220> FEATURE:
<223> OTHER INFORMATION: MDK primer2

<400> SEQUENCE: 2
agcaaggact gcggcatg                                            18

<210> SEQ ID NO 3
<211> LENGTH: 18
<212> TYPE: DNA
<213> ORGANISM: Artificial sequence
<220> FEATURE:
<223> OTHER INFORMATION: MDK primer3

<400> SEQUENCE: 3
gccacacgcc ccccagct                                            18

<210> SEQ ID NO 4
<211> LENGTH: 22
<212> TYPE: DNA
<213> ORGANISM: Artificial sequence
<220> FEATURE:
<223> OTHER INFORMATION: PTN primer1

<400> SEQUENCE: 4
gcaaatacca gttccaggct tg                                       22

<210> SEQ ID NO 5
<211> LENGTH: 25
<212> TYPE: DNA
<213> ORGANISM: Artificial sequence
<220> FEATURE:
<223> OTHER INFORMATION: PTN primer2

<400> SEQUENCE: 5
ttcttgcctt cctttttctt cttct                                    25

<210> SEQ ID NO 6
<211> LENGTH: 25
<212> TYPE: DNA
<213> ORGANISM: Artificial sequence
<220> FEATURE:
<223> OTHER INFORMATION: PTN primer3

<400> SEQUENCE: 6
gaactcacca gcccaagcct caagc                                    25

METHOD OF TREATMENT FOR ISCHEMIC HEART DISEASE

TECHNICAL FIELD

The present invention relates to a method of curing a damaged myocardium to improve cardiac function.

BACKGROUND ART

Myocardiac infarction is a condition of irreversible necrosis of heart muscle that results from prolonged ischemia. The infarct zone comprising a damaged myocardiac tissue are infiltrated with non-contracting scavenger cells and ultimately are replaced with scar tissue. This fibrous scar does not significantly contribute to the contraction of the heart. Cardiac cells do not divide to repopulate the damaged region, the region will fill with connective tissue produced by invading fibroblasts. Fibroblasts produce extracellular matrix components of which collagen is the most abundant. Neither the fibroblasts themselves nor the connective tissue form contractile tissue. Thus, molecular and cellular cardiomyoplasty research has evolved to directly address myocardial necrosis.

Conventionally, cellular cardiomyoplasty are performed by transplanting cells into the damaged myocardium with the goal of restoring its contractile function. In the methods, myoblast cells and hematopoietic stem cells are often used as the transplanting cells in order to cure the damaged myocardium. Myoblast cells are prepared by allowing the established cell lines to be induced, but such cells are typically rejected from the human recipient.

For example, Nature 428, 668-673, 2004 April, reported hematopoietic stem cells adopt only traditional hematopoietic fates based on the study of the ability of hematopoietic stem cells to regenerate myocardium in an infarct model. Also, Cell, vol. 119, Issue 4, 12 Nov. 2004, pages 543-554, reported muscle-engrafted cells from marrow and/or circulation localizes to the same anatomic compartment as myogenic satellite cells, but they displayed no intrinsic myogenicity. It further reported functional adult myogenic progenitors did not arise from hematopoietic or other bone marrow or circulating precursors.

Furthermore, molecular cardiomyoplasty has developed because fibroblasts can be genetically manipulated. For example, Tam et al., J. Thoracic and Cardiovascular Surgery, 918-924 (1995) used MyoD which is one of myogenic determination genes expressing retrovirus in vitro for fibroblast to myoblast conversion. However, its viability has not been demonstrated in vivo.

On the other hand, secreted frizzled-related protein (SFRP) family is known for having a cysteine-rich domain homologous to the putative Wnt-binding site of Frizzled proteins, and acts as soluble modulators of Wnt signaling. Among the SFRP family, SFRP2 and SFRP4 are related to signal cascade in apoptosis, which is reported in Cancer Res. 65 (3), 743-748 (2005), and J. Biol. Chem. 279 (15), 14602-14609 (2004). Furthermore, other molecules involved in apoptosis include Midkine (MDK), Pleiotrophin (PTN) and Thymosin beta-10 (TB10) (J Med Dent Sci. 46 (1):45-51 (1999), and J Biol Chem. 277 (39), 35862-8 (2002), J. Biol. Chem. 280 (40), 340003-34007 (2005)).

Pleiotrophin (PTN) and midkine (MDK) are two members of developmentally regulated cytokines showing very similar three-dimensional structure with approximately 50% identity in amino acid sequences. They are highly conserved through Drosophila to man and are originally implicated in neural development, neurodegenerative diseases and certain form of cancer. PTN and MDK are localized in the radial glial processes of the embryonic brain, along which neural stem cells migrate and differentiate (Cancer Letter. 2004; 204:127-143, and Development. 1995; 121:37-51).

Interestingly, both proteins show mitotic, anti-apoptotic, and angiogenic activities, which are the basic properties required for the regeneration of injured tissues, not only in developing neural tissues but also in adult brain (Cancer Letter. 2004; 204:127-143, Development. 1995; 121:37-51, and Gene Therapy. 2005; 12:487-493). Furthermore, some reports have suggested the expression and their reparative capabilities in injured extra-neural organs including liver and heart (Liver Int. 2004; 24:484-491, Biochem Biophys Res Commun. 2005; 332:1146-1152, and Anticancer res. 1998; 18:145-152). In addition, Anticancer res. 1998; 18:145-152 and J. Immunol. 2001; 167:3463-3469 reported that developmentally regulated cytokines, PTN and MDK, are induced in stressed adult organs such as ischemic heart and kidney.

However, the role for these molecules of SFRP2, SFRP4, MDK, PTN, and TB10 in the damaged myocardium, and their therapeutic potential for the ischemic cardiomyopathy ware not well known.

DISCLOSURE OF INVENTION

Problem to be Solved by the Invention

Accordingly, an object of the present invention is to provide a method of treatment for ischemic heart disease by promoting scar formation without fibrosis derived from host cells, and constructing tissue with elasticity, and a scar formation accelerator, and a drug for ischemic myocardial injury used therein.

Another object of the present invention is to provide a method of treatment for ischemic heart disease capable of promoting scar formation for a long time to help tissue formation in addition to improve handle ability a scar formation accelerator, and a drug for ischemic myocardial injury used therein.

Means for Solving Problem

After intensive investigations to achieve the above objects, the present inventors have found that certain molecules can promote scar and granulation formation derived from host cells to form tissues with elasticity, and thereby repair the damaged myocardiac tissue, and myocardial function can be improved. The present invention has been achieved based on these findings.

Specifically, the present invention provide a method of treatment for ischemic heart disease administering a scar formation accelerator without causing fibrosis containing at least one selected from SFRP2, SFRP4, Midkine (MDK), Pleiotrophin (PTN) and Thymosin beta-10 (TB10) as an effective ingredient to promote scar formation, and thereby repair a damaged myocardiac tissue. The scar formation accelerator may comprise at least one selected from SFRP2, SFRP4, MDK, PTN, and TB10 inserted in delivery vehicles, specifically the vehicles supported on and/or anchored to a sheet.

The present invention further provides that use of at least one selected from SFRP2, SFRP4, MDK, PTN, and TB10 for preparing a drug for the treatment of ischemic myocardial injury by promoting scar formation to repair a damaged myocardiac tissue. The drug may comprise at least one selected from SFRP2, SFRP4, MDK, PTN, and TB10 inserted in delivery vehicles, specifically the vehicles supported on and/or anchored to a sheet.

In another aspect, the present invention provides a scar formation accelerator containing at least one selected from SFRP2, SFRP4, MDK, PTN, and TB10 as an effective ingredient for use in repairing a damaged myocardiac tissue.

The present invention provides a drug for ischemic myocardial injury comprising at least one selected from SFRP2, SFRP4, MDK, PTN, and TB10 as an effective ingredient capable of promoting scar formation, and thereby repairing a damaged myocardiac tissue. The drug may comprise at least one selected from SFRP2, SFRP4, MDK, PTN, and TB10 inserted in delivery vehicles, specifically the vehicles supported on and/or anchored to a sheet.

In the present specification, an infarct zone (i.e., the damaged region of the myocardium) can be determined by one of skill in the art. Near the infarct zone means sufficiently close that damage to necrotic heart muscle is realized. Typically, it means within about 1 cm of the edge of the infarct zone.

Further objects, features and advantages of the present invention will become apparent from the following description of the preferred embodiments.

EFFECT OF THE INVENTION

According to the present invention, each of SFRP2, SFRP4, MDK, PTN, and TB10 act on host cells in and/or near the infarct zone, and the host cells by themselves contribute to form elastic tissues. Therefore, it is not necessary to use donor cells or graft tissue and is free from rejection. Specifically, in case that the effective ingredient inserted in delivery vehicles or the vehicles supported on and/or anchored to a sheet is administered, the effective ingredient slowly acts on cells in and/or near the infarct zone for a long time enough to complete scar formation with elasticity, and can improve myocardial function.

BEST MODE FOR CARRYING OUT THE INVENTION

Figure 1:
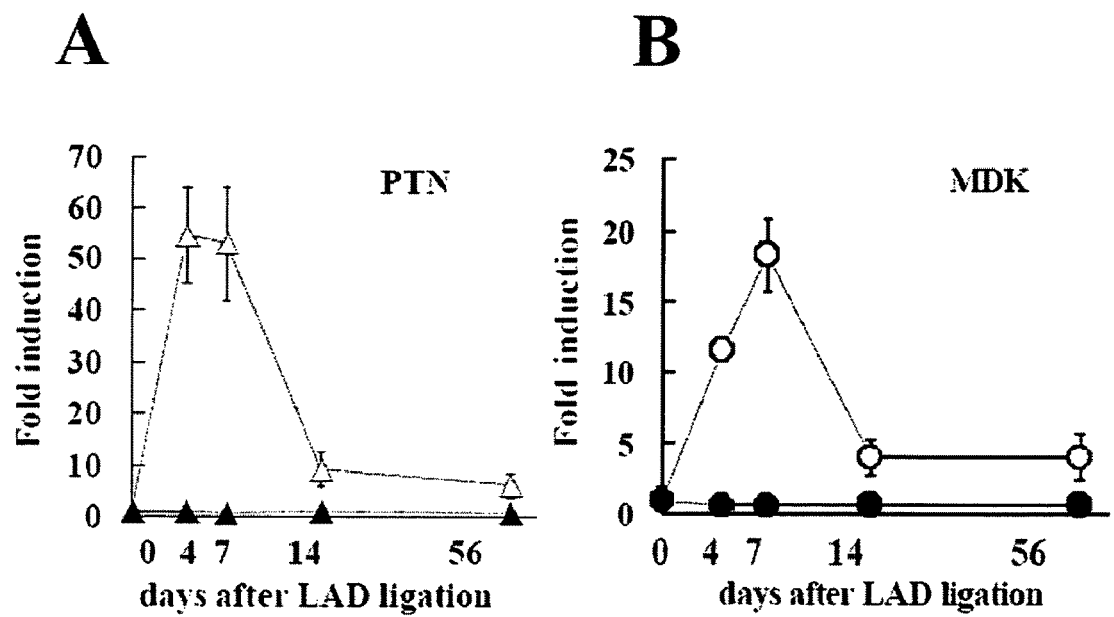
FIG. 1 is a line plot of expressions of pleiotrophin (A) and midkine (B) mRNA in infarcted (open symbols) or non-infarcted myocardium (closed symbols) LV myocardium of LAD-ligated LEW hearts of rat obtained in the Reference Example 6.

The present invention relates to a method of treatment for ischemic heart disease, and a feature of the method resides in administering a scar formation accelerator containing at least one selected from SFRP2, SFRP4, MDK, PTN, and TB10 as an effective ingredient.

Ischemic heart disease in the present invention includes, for example, acute myocardial infarction (AMI), myocardial infarction (MI), severe angina pectoris (AP), and other disease which causes necrosis of heart muscle that results from prolonged ischemia. As necrosis of heart muscle progresses, the damaged myocardiac tissue are replaced with fibrous tissue, thickness of the infarct zone gets thinner, and the cardiac inner cavity dilates, therefore cardiac function such as contractility deteriorates and results in heart failure.

The present inventors found that at least one selected from SFRP2, SFRP4, MDK, PTN, and TB10 have an effect to promote scar formation, and thereby repair the damaged myocardiac tissue. The repaired tissues comprise contractile tissues, so the cardiac function can be improved.

The scar formation accelerator contains at least one selected from SFRP2, SFRP4, MDK, PTN, and TB10 as an effective ingredient.

The present inventor found that the MDK and PTN gene expressions were rapidly induced in adult rat myocardium after infarction. The inductions were strong but transient as the expressions peaked at one week and recovered to near normal levels as early as two weeks after the infarction, when LV remodeling started to progress. Surprisingly, the injection of recombinant MDK after the LAD-ligation significantly attenuated the following LV remodeling and myocardial fibrosis. Non-infarcted myocardium was enlarged but less cardiomyocyte hypertrophy was observed in MDK-injected hearts.

The present inventor also found that the injection of recombinant SFRP4 or TB10 after the LAD-ligation significantly attenuated the following LV remodeling and myocardial fibrosis.

Hereinafter, SFRP2, SFRP4, MDK, PTN, TB10 and combination thereof are collectively referred to as "effective ingredient". The effective ingredient can be prepared by various methods as long as they are purified for use in pharmaceuticals.

The effective ingredient may be native or recombinant, and include, for example, nucleic acid; protein, polypeptide, and peptide, where at least one or more amino acid may be substituted, deleted, and other modified, as long as they are functional in patient before or after administration (hereinafter optionally referred to as "active effective ingredient"). Among them, soluble protein and polypeptide are preferred. The effective ingredient can be used alone or in combination of SFRP2, SFRP4, MDK, PTN, and TB10. The effective ingredient can be prepared by either chemical synthesis or biological synthesis according to the well-known technique. For example, a recombinant protein for use in effective ingredient can be prepared by a method of using cells capable of expression of effective ingredient stably or temporary prepared in vivo or in vitro. Such recombinant proteins are commercially available.

Furthermore, the gene sequence of the nucleic acid including nucleic acid encoding the active effective ingredient is available from a variety of sources including GenBank (Los Alamos National Laboratories, Los Alamos, N. Mex.). The nucleic acid can be obtained by restriction endonuclease digestion and isolation of a gene fragment, or by polymerase chain reaction (PCR) to amplify cDNA copies of mRNA from cells expressing the gene of effective ingredient. The nucleic acid is generally inserted into, for example, recombinant vectors such as plasmid DNA vectors, cDNA-containing liposomes, modified viruses, or nanoparticles together with regulatory elements such as promoter (e.g. cardiac tissue-specific promoter-enhancer), polyadenylation signal and enhancer by standard techniques known to those of ordinary skill in the art in order to provide a recombinant nucleic acid which is functional in a patient.

The scar formation accelerator may comprise other components, which are conventionally used in the pharmaceutical agents. Such components include, for example, delivery vehicles, carriers, excipients, chelating agents, nonionic surfactants, buffers, stabilizers, and those used in pharmaceutical field, which are nontoxic to the cell or mammal being exposed thereto at the dosages and concentrations employed.

For example, the scar formation accelerator of the present invention may be aqueous solution comprising the active effective ingredient dissolved in buffer, which can be administered by intravenus injection, topical injection into infarct zone.

The scar formation accelerator may be provided as liquid, powder, granule, capsules, tablets, pills, and other molded bodies, which additionally may be prepared with enteric coatings such as cellulose acetate phthalate.

Typical examples of the scar formation accelerator of the present invention include at least one selected from SFRP2, SFRP4, MDK, PTN, and TB10 inserted in delivery vehicles. The delivery vehicles, is not limited to as long as they can deliver the effective ingredient, and include polymer matrix and liposome (e.g., lipid bilayer) in addition to cells and virus in the form of transformed with recombinant nucleic acid. The polymer matrix includes one or more synthetic or natural polymers and can be a biostable or a bioabsorbable polymer. The bioabsorbable polymer may be natural or synthetic and includes, for example, collagen, hydrogel (e.g. agar, gelatin), fibrin, albumin, cellulose, starch, chitin, chitosan, hyaluronic acid, and other protein, poly-sugars; polylactic acid (PLA), polyglycolic acid (PGA), poly lactic/glycolic acid (PLGA), polycyanoacrylate, and other synthetic polymers or polypeptide; and wide variety of others typically disclosed as being useful in implantable or delivery medical devices. Among them, substances such as collagen having an excellent biocompatibility and handling ability are preferred. In the present specification, the bioabsorbable polymer means polymers including biodegradable polymer.

The effective ingredient encapsulated in hydrophilic polymers such as hydrogel and collagen is preferred, because they can easily control a releasing rate and term of the effective ingredient. Specifically, effective ingredient encapsulated in gelatin or mixed with collagen can be used as a slow-releasing agent for a long time.

The scar formation accelerator can be administered by itself or as a part of a pharmaceutical composition (or medicament) that further comprises one or more carriers such as spherical particles, films, and sheet, diluents, wetting or suspending agents, adjuvants, active ingredients, and other components used in pharmaceutical field. When the scar formation accelerator is administered as part of a combination therapy, the other agent(s) of the combination may also be contained in the same pharmaceutical composition or as a part of a separate pharmaceutical composition or both.

In the present invention, the scar formation accelerator can be constituted by recombinant protein of at least one selected from SFRP2, SFRP4, MDK, PTN, and TB10, specifically SFRP4, MDK and TB10. Such agents can be directly injected into infarcted area to prevent progression of the remodeling in dose-dependent fashion.

Typical examples of the scar formation accelerator of the present invention further include at least one selected from SFRP2, SFRP4, MDK, PTN, and TB10 inserted in delivery vehicles supported on and/or anchored to a sheet. Such sheet plays the role of scaffold, when cells in and/or near the infarct zone aggregate and form tissue. Additionally, the sheet makes administration easier because of its handleability.

The sheets can be made of bioabsorbable (biodegradable) polymer as stated above. The bioabsorbable polymer can be selected depending on desired polymer stability, and specifically, PLA, PGA, and PLGA are preferred due to its biocompatibility and wide range of biodegradable properties. The main degradation products of PLA, PGA, and PLGA, lactic and glycolic acids can be cleared quickly within the human body. Moreover, the degradability of these polymers can be adjusted from months to years depending on its molecular weight and composition. The PLA, PGA, and PLGA in the present specification mainly comprises monomer unit corresponding to lactic acid and/or glycolic acid, and may further comprise other monomer unit as long as they have desired absorbability (degradability).

The route of administration is in accord with known methods, e.g. injection or infusion by intravenous, intramuscular, intraarterial or intralesional routes, topical administration, or by slow release (sustained release) systems, and preferably, intralesional routes in use of slow release systems. On the other hand, continuous intravenous administration would be easier and/or safer, and is also preferred. Typical example of the slow release systems comprises that 1 μg of effective ingredient proteins can be continuously released for more than 1 day, usually up to 1 week.

Dosages and desired effective ingredient concentrations in the scar formation accelerator of the present invention may vary depending on the particular use envisioned. The determination of the appropriate dosage or route of administration is well within the skill of an ordinary physician. In case of topical administration by injection, the amount of the active effective ingredient is, for example, from about 0.1 to 100 μg/cm$^2$, preferably from 0.5 to 50 μg, per square centimeter. In case of topical administration using active effective ingredient supported on and/or anchored to a sheet, the amount of the active effective ingredient is, for example, from about 1 to 500 ng/cm², preferably from 5 to 200 ng/cm², relative to the area of the sheet.

The timing of administration can be appropriately selected depending on the kinds of effective ingredient and the role they have. For example, earlier administration of MDK after MI such as before the completion of cardiomyocyte death could induce a more dramatic effect.

Furthermore, in the present invention the effective ingredient can be used for preparing of a drug for the treatment of ischemic myocardial injury by promoting scar formation to repair a damaged myocardiac tissue. The drug for ischemic myocardial injury may comprise at least one selected from SFRP2, SFRP4, MDK, PTN, and TB10 as an effective ingredient, and the composition, the form, how to administer, and other materials and technique are the same as stated above.

Preferred embodiment of the present invention are the process comprising transplanting a sheet to the infarct zone, wherein the sheet comprises protein of at least one selected from SFRP2, SFRP4, MDK, PTN, and TB10 encapsulated in gelatin and supported on and/or anchored to a biodegradable PLGA sheet in the amount of 50 ng/cm².

Another preferred embodiment of the present invention are the process comprising administrating by injection of an agent to the infarct zone or the, wherein the agent comprises a recombinant protein of at least one selected from SFRP2, SFRP4, MDK, PTN, and TB10 in collagen gel, such as agent having 25 μg of the each protein in 200 μl collagen.

According to the present invention, scar formation is promoted by the effect of effective ingredient in and/or near the infarct zone, thickness of the infarct zone is increased for about two to three weeks and no dilation of the cardiac inner cavity is occurred. The scar comprises not fibrous tissue but cells having contractility. As a result, cardiac function such as contractility is improved and can prevent from heart failure.

Cardiac remodeling after MI, which is clinically defined by changes in left ventricular size, shape, and function, appears initially compensatory but generally adverse and linked to heart failure progression. Histologically, cardiomyocyte hypertrophy and interstitial fibrosis are usually observed in the remodeled hearts and the extent of the ventricular enlargement correlates with poor prognosis of the patients with coronary artery disease (Circulation. 1990; 81: 1161-72, Am J Cardiol. 2003; 93(suppl):17B-20B, Lancet. 2006; 367:356-367). Thus, it is now widely believed that ventricular remodeling is an important therapeutic target in patients with MI.

Cardiac remodeling can be observed as attenuating the following LV remodeling and myocardial fibrosis. Namely, non-infarcted myocardium was enlarged but less cardiomyocyte hypertrophy was observed.

The ability of scar formation without fibrosis can be also determined by measuring the thickness of the infarct zone by ultrasound. For example, the thickness of the infarct zone is recovered up to, for example, at least half, preferably more than 70% relative to normal thickness, provided that the infarct zone comes in contact with a sheet anchoring 50 ng/cm² of the effective ingredient continuously for four weeks.

The present inventors examined the gene expression profile of the cells constituting the newly formed tissue in the infarct zone, and did not find prominent increase in expression of either myogenic gene such as MyoD, myf5 and myogenin, or cardiac specific gene such as GATA4, Nkx2-5, and cTn-T. Namely, effective ingredient may promote a generation of neither skeletal muscle tissue nor myocardial tissue in the infarct zone. The mechanism of improvement cardiac function by administrating effective ingredient comprising SFRP2, SFRP4, MDK, PTN, and/or TB10 is not clear, but it would seem that the effective ingredient recruits undifferentiated mesenchymal cells to and/or near by the infarct zone to differentiate and to form tissue with elastic property.

EXAMPLES

The present invention will be illustrated in further detail with reference to several examples and comparative examples below, which by no means limit the scope of the invention.

Reference Example 1

(Making of Myocardial Infarction Model Rat)

Wistar-Lewis rats [180-220 g; 6-10 weeks old; Seac Yoshitomi Ltd, Fukuoka, Japan (SD Rats, Nippon Crea, Japan)] were used in this experiment. All rats received humane animal care in compliance with the "Principles of Laboratory Animal Care," formulated by the National Society for Medical Research, and the "Guide for the Care and Use of Laboratory Animals," prepared by the National Institutes of Health (NIH Publication No. 85-23, revised 1996). SD Rats were anesthetized by intraperitoneal injection of pentobarbital (50 mg/kg body weight). The anesthetized rats were intubated and positive-pressure ventilation was maintained with a ventilator (model SN-480-7, Shinano, Tokyo, Japan). The heart was exposed through a 2.5-cm left lateral thoracotomy. Left Anterior Descendant main branch was ligated at segment 7 with 6.0 proline surgical tread (LAD ligation) for myocardial infarction model. Hereinafter, rats 2 weeks post LAD ligation are often called "model rat".

Reference Example 2

(Making of Myocardial Infarction Model Rat)

Male Lewis rats at eight weeks of age (220-250 g; Seac Yoshitomi Ltd. Fukuoka, Japan) were used. All the animals received humane animal care under the Guidelines on Animal Experiments of Osaka University Graduate School of Medicine and the Japanese Animal Protection and Management Law. The Osaka University Institutional Animal Research Committee reviewed and approved the study protocol. The rats were anesthetized with ketamine (90 mg/kg) and Xylazine (10 mg/kg) and myocardial infarction was produced by ligation of the left anterior descending coronary artery (LAD) under mechanical ventilation as reported (Circulation. 1988; 78:186-201), and the rats are often called "LAD-ligated rats". The rats 2 weeks post LAD ligation are often called "model rat".

Reference Example 3

(Myoblast Injection Model)

Myoblasts were isolated from the skeletal muscles of the posterial limbs of SD rat. The rats were euthanized and the muscles were excised and washed with phosphate-buffered saline (PBS). After meticulous removal of the non-muscular tissues, the muscles were minced and enzymatically digested with 5 mg/mL of collagenase (Gibco BRL, Rockville, Md.) at 37 degrees for 40 minutes. After treatment, the cells were collected and resuspended in DMEM (Gibco BRL) with 20% FBS and 1% penicillin-streptomycin (Gibco BRL). The initial plating was performed in 100-mm collagen-coated culture dishes (IWAKI, Tokyo, Japan), and the cells were cultured at 37 degrees in a humidified atmosphere containing 5% $CO_2$. The next day, unattached cells were removed by changing the culture medium, and the cells were grown to about 70% confluence. After five days of culture, the cells were harvested, washed with DMEM, and kept on ice until transplantation. Usually, $20\times10^6$ myoblast cells were obtained from one rat, and the cultured cells contained around 50% desmin-positive cells. The myoblast was used in the formation of myoblast sheet of Reference Example 4.

0.2 mL of the myoblast cell suspension (including $5\times10^6$ of cultured cells) was injected with a 30 G tuberculin syringe into one site in the RV and 3 sites in the LV wall (anterior free wall, apex, and posterior wall) each of six model rats prepared in Reference Example 1. One week after the treatments, the treated rats were sacrificed to obtain heart sample (hereinafter often called group D) for Gene Chip analysis.

Reference Example 4

(Myoblast Sheet Model)

The myoblast isolated in Reference Example 1 was feed on a tissue culture dish coated with thermoresponsive polymers, poly-N isopropylacrylamide (PIPAAm) (Procell, Cell Seed Co., Tokyo, Japan) to fabricate a myoblast sheet, wherein the surfaces of these dishes is hydrophobic at 37° C. and become hydrophilic at temperature lower than 20° C. The cells suspensions with a density of $5\times10^6$ in 6 cm dish were cultured with DMEM supplemented 20% FBS at 37° C., 5% $CO_2$ for 1-2 days. The confluent cells cultured on the 6 cm dish are spontaneously detached by placing them at 20° C. for one hour to form 1.5 cm×2.0 cm size myoblast sheet.

The obtained myoblast sheet was transplanted on the surface of infracted area each of six model rats prepared in Reference Example 1. One week after the treatments, the treated rats were sacrificed to obtain heart sample (hereinafter often called group E) for Gene Chip analysis.

Reference Example 5

(Gene Chip Analysis)

Six rats [Wistar-Lewis rats (180-220 g; 6-10 weeks old; Seac Yoshitomi Ltd, Fukuoka, Japan (SD Rats, Nippon Crea, Japan)] were sacrificed to obtain heart untreated sample for a control (hereinafter called group A).

Likewise, six model rats (2 weeks post LAD ligation) prepared in Reference Example 1 were sacrificed to obtain heart sample (hereinafter called group B).

1.5×2.0 cm collagen sheet (Ø33 mm, Kokencellgen, Tokyo, Japan) was transplanted on the surface of infracted area each of six model rats prepared in Reference Example 1. One week after the treatments, the treated rats were sacrificed to obtain heart sample (hereinafter called group C).

2 samples of one from non-ischemic area and the other from ischemic or treated area of the heart were collected for each group (A, B, C, D, E) and followed by RNA extraction for gene expression analysis with Gene Chip Rat version (Affymetrix Calif., USA). Furthermore, data mining was performed provided that gene expression profiles ischemic area of Group E higher than the other groups using GeneSpring7 software, and finally, SFRP2, SFRP4, Midkine, pleiotrophin, and Thymosin beta 10 were found.

Reference Example 6

Infarcted and non-infarcted left ventricular (LV) myocardia from the model rats prepared in the reference example 2 were removed at 4, 7, 14, or 56 days after the ligation and immediately stored in RNAlater (Trade Mark) solution (QIAGEN, Hilden, Germany) until use (n=5 for each time points). Native myocardia from fifteen normal rats were also removed and used as references. Total RNA was extracted with RNeasy mini kit (QIAGEN) and the relative levels of PTN or MDK gene transcripts were measured by real-time quantitative RT-PCR technique using ABI PRISM 7700 Sequence Detection System (J Heart Lung Transplant. 2002; 21:1090-1100). The nucleotide sequences for the forward primers, reverse primers and TaqMan probes (Trade Mark) used were as follows:

```
rat MDK;
                                 (sequence number 1)
    CGG ATG GTC TCC TGG CAC, (sequence number 2)
    AGC AAG GAC TGC GGC ATG, (sequence number 3)
    GCC ACA CGC CCC CCA GCT, rat PTN;
                                 (sequence number 4)
    GCA AAT ACC AGT TCC AGG CTT G, (sequence number 5)
    TTC TTG CCT TCC TTT TTC TTC TTC T, (sequence number 6)
    GAA CTC ACC AGC CCA AGC CTC AAG C.
```

The averaged copy number of gene transcripts in each sample was normalized to GAPDH and the fold induction of a gene was calculated using the formula: Fold induction=normalized value in a sample after MI/average of the normalized value in the above-identified reference myocardia from normal LEW rats.

In the result, low but detectable level of PTN or MDK mRNA was expressed in normal rat myocardium (PTN/GAPDH: 0.0021±0.00028, MDK/GAPDH: 0.00083±0.000080, n=15) and the expressions of both genes were induced after the myocardial infarction (FIG. 1A, B). The induction of PTN or MDK gene expression was peaked 4 or 7 days after the LAD ligation, respectively, and both of them were rapidly decreased 14 days after the ligation. The strong inductions were observed in infarcted myocardium but not in non-infarcted myocardium. PTN or MDK mRNA in the ischemic area was increased roughly 54- or 18-fold if compared to the average of the normalized value from naive LEW rats. Immunohistochemical analysis revealed that MDK expression was observed in surviving cardiomycytes in border-zone and infracted areas but not in non-infarcted area (data not shown) and this result was consistent with the previous observation made at the earlier time points after MI (Anticancer res. 1998; 18:145-152). In immunohistochemical staining for MDK protein, MDK appears to express on surviving cardiomyocytes in border-zone and infracted area but it was not expressed in non-infarcted area of the heart after MI.

Example 1

1 μg of SFRP2 manufactured by R&D system is mixed with 10 mg of gelatin (Nitta Gelatin, Japan) to form slow releasing gel microspheres 100-150 um in diameter. The gel pellets are placed in the bio-degradable PLGA sheet 2 cm×2 cm in size (scaffold sheet; "Resomer RG858", "Resomer768"

manufactured by Boehringer Ingelheim) and transplanted on the surface of ischemic rat heart 2 weeks post LAD ligation.

Examples 2 to 5

The procedure of Example 1 is repeated, except for using 1 μg of SFRP4 (Example 2), 1 μg of Midkine (Example 3), 2 μg of pleiotrophin (Example 4), those manufactured by R&D system, or 1 μg of Thymosin beta 10 (Example 5) manufactured by Sigma, instead of SFRP2. The gel microspheres are placed in the bio-degradable PLGA sheet 2 cm×2 cm in size [same as Example 1] and transplanted on the surface of ischemic rat heart 2 weeks post LAD ligation.

Comparative Example 1

The procedure of Example 1 is repeated, except to form gel microspheres 100-150 um in diameter without SFRP2. The gel microspheres are placed in the bio-degradable PLGA sheet 2 cm×2 cm in size [same as Example 1] and transplanted on the surface of ischemic rat heart 2 weeks post LAD ligation.

Example 6

(Direct Injection Therapy)
SFRP2 solution containing 2 ug of SFRP2 manufactured by R&D system dissolved in PBS is administered to ischemic rat heart 2 weeks post LAD ligation, with 30 G needle (Termo, Tokyo, Japan) injection at 6 points under left thoracotomy operation or one shot intra-peritoneal administration.

Examples 7 to 10

The procedure of Example 6 is repeated, except for using 1 μg of SFRP4 (Example 7), 1 μg of Midkine (Example 8), 2 μg of pleiotrophin (Example 9), those manufactured by R&D system, or 1 μg of Thymosin beta 10 (Example 10) manufactured by Sigma, instead of SFRP2.

Example 11

The procedure of Example 6 is repeated, except for using a cocktail of 2 μg of SFRP2, 2 μg of SFRP4, 1 μg of Midkine, 4 μg of pleiotrophin, those manufactured by R&D system, and 1 μg of Thymosin beta 10 (Example 10) manufactured by Sigma, instead of SFRP2.

Comparative Example 2

The procedure of Example 3 is repeated, except for PBS instead of SFRP2 solution to administer it to ischemic rat heart 2 weeks post LAD ligation.

Example 12, 13, 14 and Comparative Example 3

Using a model rat prepared in the reference example 2, said rat 2 weeks post LAD ligation, baseline cardiac functions were measured and the infarcted rats were treated by injecting various amounts of recombinant human PTN or MDK (R&D systems Inc., Minneapolis, Minn.) into four sites of border-zone myocardium (n=10 for each subgroup). The injections were performed by re-opening left thorax of the animals under the similar anesthesia. The cytokines were given 1, 5, or 25 μg of the each protein in 200 μl collagen using a 30 G needle as previously described (Nature. 2005; 432:466-472) as Example 12, 13, and 14 respectively and control rats received collagen gel alone as Comparative Example 3

Example 15, 16 and Comparative Example 4

Using a model rat prepared in the reference example 1, said rat 2 weeks post LAD ligation, baseline cardiac functions were measured and the infarcted rats were treated by injecting various amounts of recombinant human SFRP2 or SFRP4 (R&D systems Inc., Minneapolis, Minn.) into four sites of border-zone myocardium (n=10 for each subgroup). The injections were performed by re-opening left thorax of the animals under the similar anesthesia. The cytokines were given 4 or 20 μg of the each protein in 200 μl collagen using a 30 G needle as previously described (Nature. 2005; 432: 466-472) as Example 15 and 16 respectively and control rats received PBS in collagen as Comparative Example 4.

Example 17 and Comparative Example 5

Using a model rat prepared in the reference example 1, said rat 2 weeks post LAD ligation, baseline cardiac functions were measured and the infarcted rats were treated by injecting various amounts of recombinant human thymosin β10 (R&D systems Inc., Minneapolis, Minn.) into four sites of border-zone myocardium (n=10 for each subgroup). The injections were performed by re-opening left thorax of the animals under the similar anesthesia. The cytokines were given 4 or 20 μg of the thymosin β10 in 200 μl collagen using a 30 G needle as previously described (Nature. 2005; 432:466-472) as Example 17 and control rats received PBS in collagen as Comparative Example 5.

Evaluation
Histological Examinations

From transplanted or injected rats each of Examples 1 to 10 and Comparative Examples 1 and 2 hearts are recovered, and transverse sections of the hearts (2-μm thick) are fixed with 10% buffered formalin, embedded in paraffin, and subjected to Hematoxylin and Eosin (H.E.) and Masson's trichrome staining.

Anti-factor VIII-related antigen coupled with horseradish peroxidase (EPOS Anti-Human von Willebrand factor/HRP, DAKO, Carpinteria, Calif.) is used to detect vascular endothelial cells in accordance with the manufacturer's protocol. To stain cells in the infract zone, specimen blocks are sectioned and immunostained with following antibodies: Monoclonal Anti-Skeletal Myosin antibody to fast-twitch skeletal-Myosin Heavy Chain (MHC, MY-32, Sigma, USA); Monoclonal Anti-Myosin (Skeletal, Slow) directed against skeletal slow MHC isoforms (NOQ7.5.4D, Sigma, Mich., USA) Each immuno-staining slide is viewed with fluorescent microscope (IX-71, Olympus, Japan).

More than five sections are prepared for each specimen. The percentage of the total fibrotic area, as determined by Masson's trichrome staining, is calculated by image analysis of the sections using a planimetric method with Windows MetaMorph software (Universal Imaging Corporation, Downingtown, Pa.).

The number of factor VIII-positive arteries and capillaries that were less than 100 μm in diameter was counted under microscope (IX-71, Olympus, Japan) at ×100 magnification.

Fibrotic area will be hardly found in the improved heart of Examples 1 to 10, while fibrosis will occurred widely in the infarct zone of Comparative Examples 1 and 2.

Histological Examinations 2

Regarding the rats of Examples 12 to 14 and Comparative example 3, six weeks after the injection, all the treated hearts were stopped at diastole by the infusion of cold cardioplegia (5% glucose solution containing 24 mEq/L potassium) and removed. They were horizontally sectioned at the center of the infarcted area. All the samples were fixed with 10% buffered formalin and paraffin-embedded. Usual Hematoxylin-Eosin (HE) and Masson's trichrome staining were routinely performed and picro-sirius red staining for the assessment of myocardial fibrosis or periodic acid-Schiff (PAS) staining for that of cardiomyocyte hypertrophy was done for the specific treatment groups as described (Hypertension. 2005; 46:412-418, Circ Res. 2002; 90:d641-648). Quantitative morphometric analysis for each staining was performed with MacScope software (MITANI Corporation, Tokyo, Japan).

Myocardial fibrosis in non-infarcted area was expressed as % fibrosis that means a fraction of collagen-rich red stained area in total myocardium, which was made from ten fields per a section per an animal. For myocyte cell size, we randomly selected 10 fields in each ventricle, and 5 myocytes were randomly chosen in each field, which were made at a magnification of ×400. Averaged results from the ten hearts in each group were shown. In addition, deparaffinized 2-μm-thick sections from the hearts 6 weeks after the injections were stained for von Willebrand factor to assess vascular density for each treatment group. Primary antibody against von Willebrand factor (A0082, Dako, Glostrup, Denmark) was used for the staining.

Assessment of MDK Expression Shown in FIG. 1

Hearts of rats obtained in the Reference Example 6 were removed one week after LAD-ligation and stored at −80° C. (n=5). 5-μm-thick frozen sections were incubated with polyclonal goat anti-rat MDK serum (sc-1398, Santa Cruz Biotechnology, Santa Cruz, Calif.) and visualized using ABC kit (ABC KIT, Vector Laboratories, Burlingame, Calif.) (Circulation. 2002 (suppl I); 106:I-264-I-269).

Figure 3:
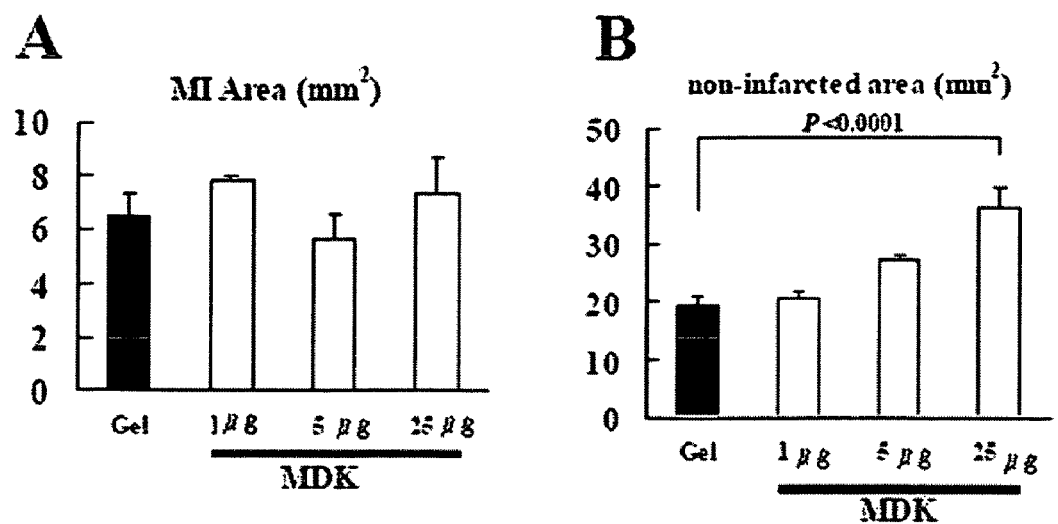
FIG. 3 is a bar graph of infracted scar area (A) or non-infarcted muscle area (B) of gel-treated or MDK-treated hearts of the rats obtained in Examples 12 to 14 and Comparative Example 3 by computer-assisted morphometric analysis.

Assessment of LV Remodeling Shown in FIG. 3

In the result, gross appearance of the hearts treated with gel alone or 25 μg of recombinant MDK were obtained (data not shown). In the short-axis sections at the center of myocardial infarction, the infarcted scar area stained with blue dye was thinner and longer in the gel-alone-treated group due to the enlargement of LV cavity but the total MI areas calculated were not significantly affected by any dose of MDK injected (FIG. 3A). On the other hand, non-infarcted myocardium of 25 μg of MDK-injected hearts appeared to be thick and, in fact, non-infarcted area of the MDK-injected hearts was significantly larger than that of gel-injected hearts (FIG. 3B). The increase of the non-infarcted area in MDK-treated hearts was MDK-dose-dependent and this dose dependent enlargement of the non-infarcted area was compatible with the echocardiographic findings shown in FIG. 2D.

Figure 4:
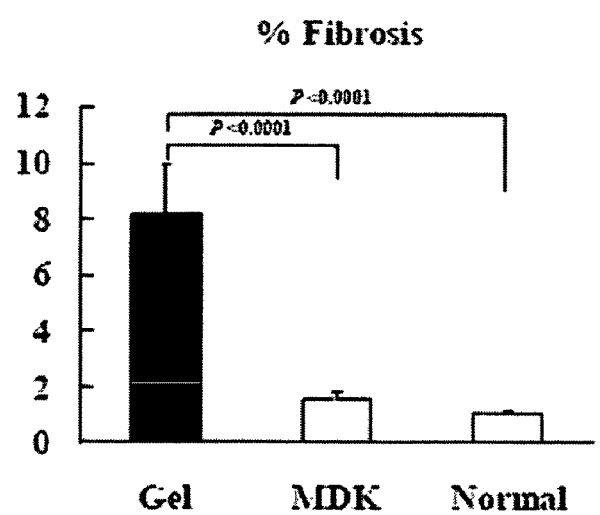
FIG. 4 is a bar graph of percent fibrotic area in the gel-treated (gel) or MDK-treated (MDK) infarcted hearts, and non-infarcted normal hearts (normal) of the rats obtained in Examples 14 and Comparative Example 3.

Assessment of Myocardial Fibrosis Shown in FIG. 4

In microscopic evaluation with picro-sirius red staining (data not shown), strong fibrotic changes were observed in non-infarcted myocardium of the gel-treated control hearts, probably reflecting a maladaptive response of the LV remodeling after the infarction. Myocardial fibrosis was also present in the MDK-treated hearts but it was significantly less if compared to that in the gel-treated control hearts (FIG. 4).

Figure 5:
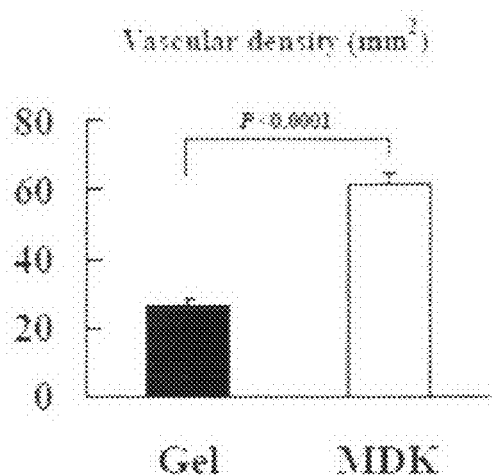
FIG. 5 is a bar graph of vascular density in the infarcted scar and the border area between the rats obtained in Examples 14 and those in Comparative Example 3.

Assessment of Vascular Density Shown in FIG. 5

In addition, since angiogenic potential of MDK was reported previously, we assessed vascular density of gel-alone treated and 25 μg of MDK-treated hearts (data not shown). After the myocardial infarction, von Willebrand factor-positive vessels were predominantly observed in the infarcted scar and border-zone areas of the gel- or MDK-treated hearts and the vascular density in the border-zone and infracted scar was significantly greater in the MDK-treated hearts than that in the gel-treated hearts (FIG. 5). The numbers of vessels in the non-infarcted area were relatively scarce and it was not possible to reliably compare the numbers between the gel-treated and MDK-treated hearts.

Wall Thickness

According to visual evaluation of the above-prepared tissue section, the wall thickness of infarct zone in Examples 1 to 10 is improved, but thickness in Comparative Examples 1 and 2 gets thinner, and the cardiac inner cavity dilates. Specifically, the improved thickness of Examples 1 to 5 is superior to that of Examples 6 to 10.

Cardiac Function

Echocardiograph measurement of transplanted or injected rats each of Examples 1 to 10 and Comparative Examples 1 and 2 is performed under anethesia with isoflurane by echocardiograph SONO 5500 commercially available by Agilent Technologies, USA using 12-MHz annular array transducer as follows.

After measurement of the body weight of the rat, anethetic is applied to the rat, and followed by maintaining for 20 minutes to stabilize the hemodynamics before the examination. M-mode echocardiograms are recorded and the heart rate (HR), left ventricular end-systolic dimension (Ds), left ventricular end-diastolic dimension (Dd), and fractional shortening (FS) are determined within about 10 minutes. The echocardiograph reader is blinded to the study group.

According to the above procedure, the echocardiograms are recorded each week up to 6 weeks later.

In the result, the contractility of the hearts of Examples 1 to 10 is improved, while that of Comparative Examples 1 and 2 is abnormal.

Figure 2:
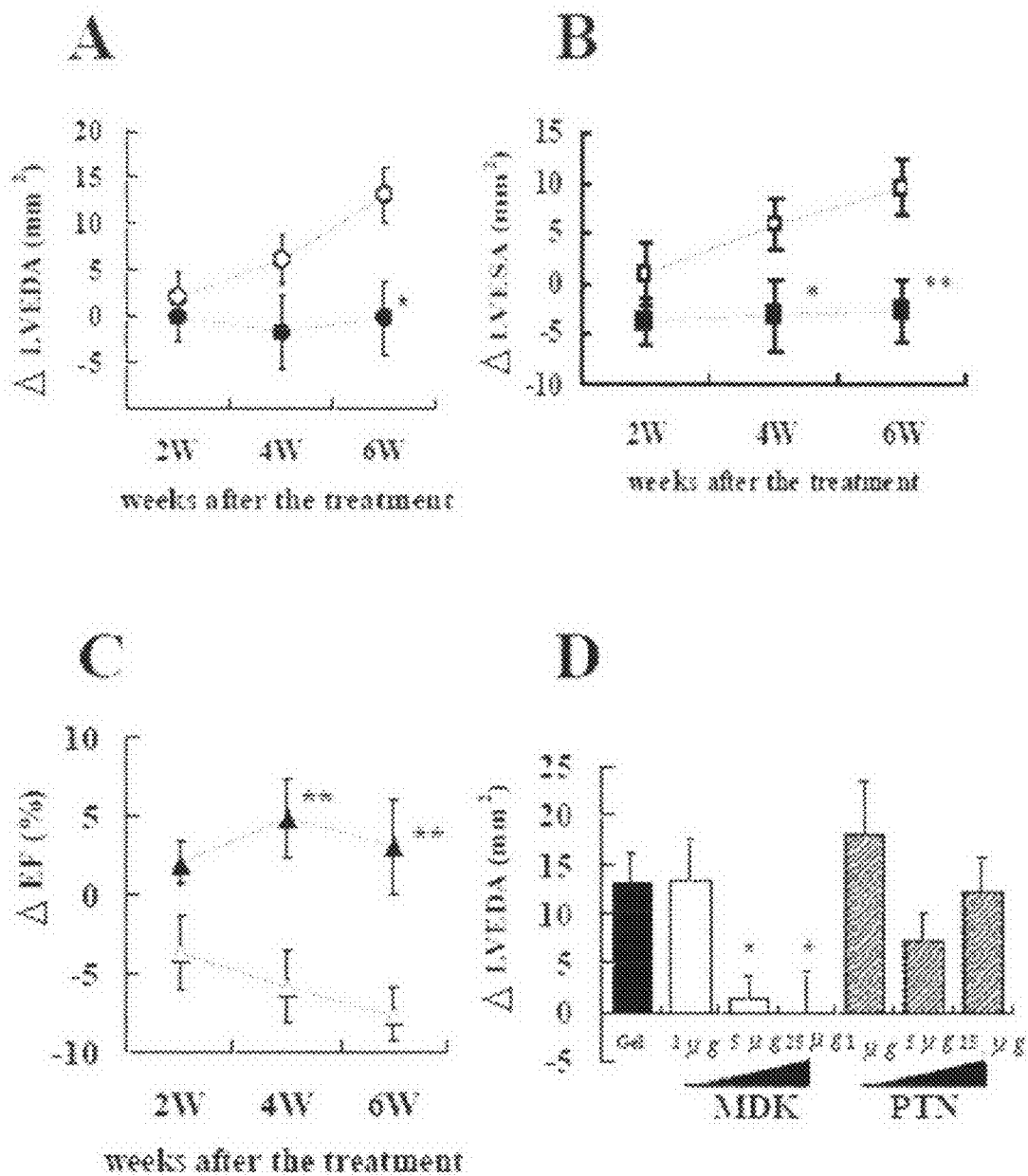
FIG. 2 is a line plot of increments of LV end-diastolic area: LVEDA (A), LV end-systolic area: LVESA (B), or Ejection fraction: EF (C) from baseline measurements of gel alone-treated rats of Comparative Example 3 (open symbols) or MDK-treated rats of Example 14 (closed symbols), and a bar graph of increments of LVEDA (D) from baseline measurements of gel alone-treated, MDK- or PTN-treated rats at six weeks after the treatment based on echocardiographic assessments.

Ehocardiographically MONITORED SHOWN in Table 1, FIG. 2

On the other hand, LV functions of the treated rats of Examples 12 to 14 and Comparative Example 3 were echocardiographically monitored 2, 4, and 6 weeks after the cytokine injection in comparison with those before the injection (baseline) under the stable hemodynamic conditions (Table 1). The cardiac ultrasonography was recorded with SONOS 5500 (Agilent Technologies, Palo Alto, Calif.) using a 12-MHz annular array transducer under anesthesia with diethyl ether. The hearts were imaged in short-axis 2D views at the level of papillary muscles and LV end-systolic area (LVESA), LV end-diastolic area (LVEDA), LV dimensions at end-systole and end-diastole (LVDs, LVDd) were determined. Ejection fraction (EF) were calculated by Pombo's method as EF (%)={(LVDd$^3$−LVDs$^3$)/LVDd$^3$}×100. Heart rate (HR) and blood pressure (BP) of the rats were continuously recorded with a Model MK-2000 BP monitor (Muromachi Kikai, Tokyo, Japan) using the indirect tail cuff method during the measurements. The LVEDA, LVESA, EF, HR, and mean BP at baseline were not significantly different among the seven groups.

In Gel-alone-treated control group, both LVEDA and LVESA were gradually increased and the difference from the baseline reached significance at 6 weeks (Table 1, FIG. 2 A, B). The EF of the control hearts constantly decreased from two to six weeks after the treatment (FIG. 2C). In contrast, the increments of LVEDA and LVESA of 25 μg of MDK-treated hearts were minimum and they were significantly smaller than those observed in control hearts (FIG. 2 A, B). In addition, the EF of the MDK-treated hearts at 4 or 6 weeks was significantly better than that of control hearts. This effect of inhibiting LV remodeling after myocardial infarction was dependent on the amount of MDK injected but similar effects were not observed by PTN injection at least up to the dose of 25 μg per a heart (FIG. 2D, Table 1).

Statistic Analysis

All data are expressed as the mean +/− standard error (SE) Time course data of cardiac functions were subjected to two-way repeated measurement multiple analyses of variance (ANOVA) using StatView 5.0 (Abacus Concept, Berkely, Calif.), and unpaired Student's t test was used to verify the difference between the indicated groups. Other comparisons were performed by one-way ANOVA with Bonferroni's posthoc test or unpaired Student's t test. P-values less than 0.05 were considered significant.

The authors had full access to the data and take responsibility for its integrity. All authors have read and agreed to the manuscript as written.

Figure 6:
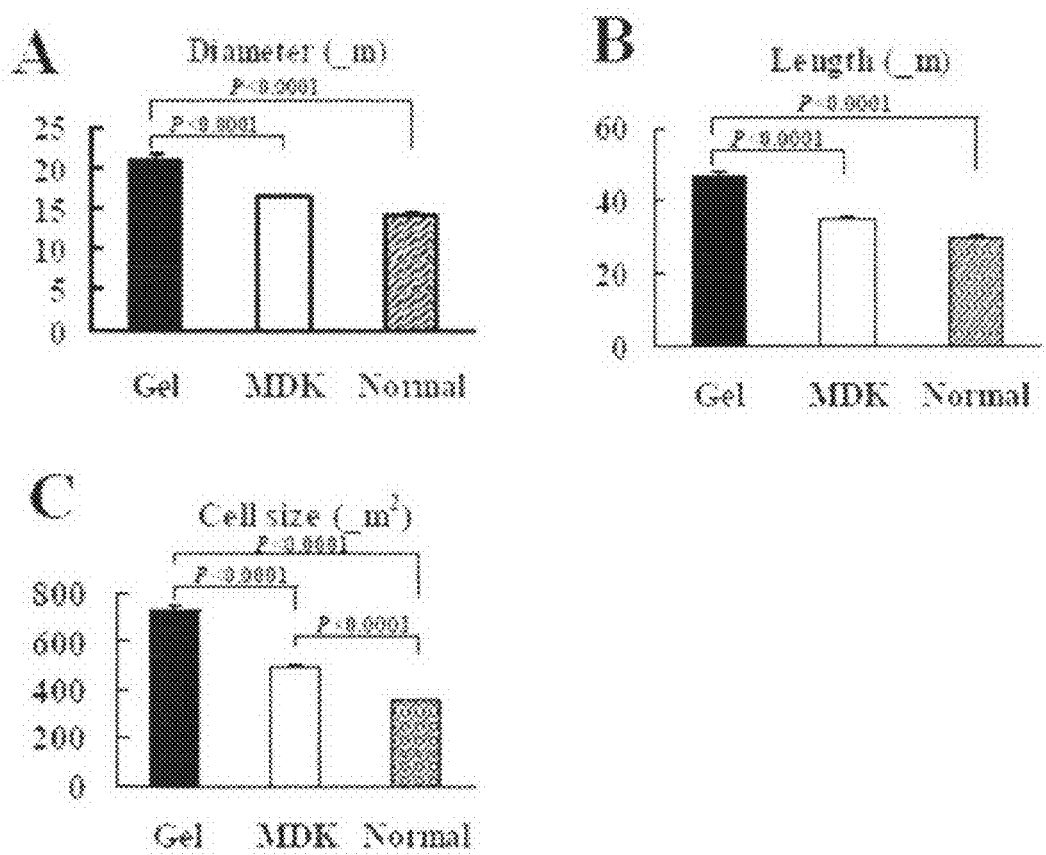
FIG. 6 is a bar graph of the cardiomyocyte width (A), length (B), and cell size (C) of the gel-treated (gel) or MDK-treated (MDK) infarcted hearts, wherein the former is obtained from Comparative Example 3, and the latter is obtained by Example 14, and non-infarcted normal hearts (normal) of the rats.
Figure 7:
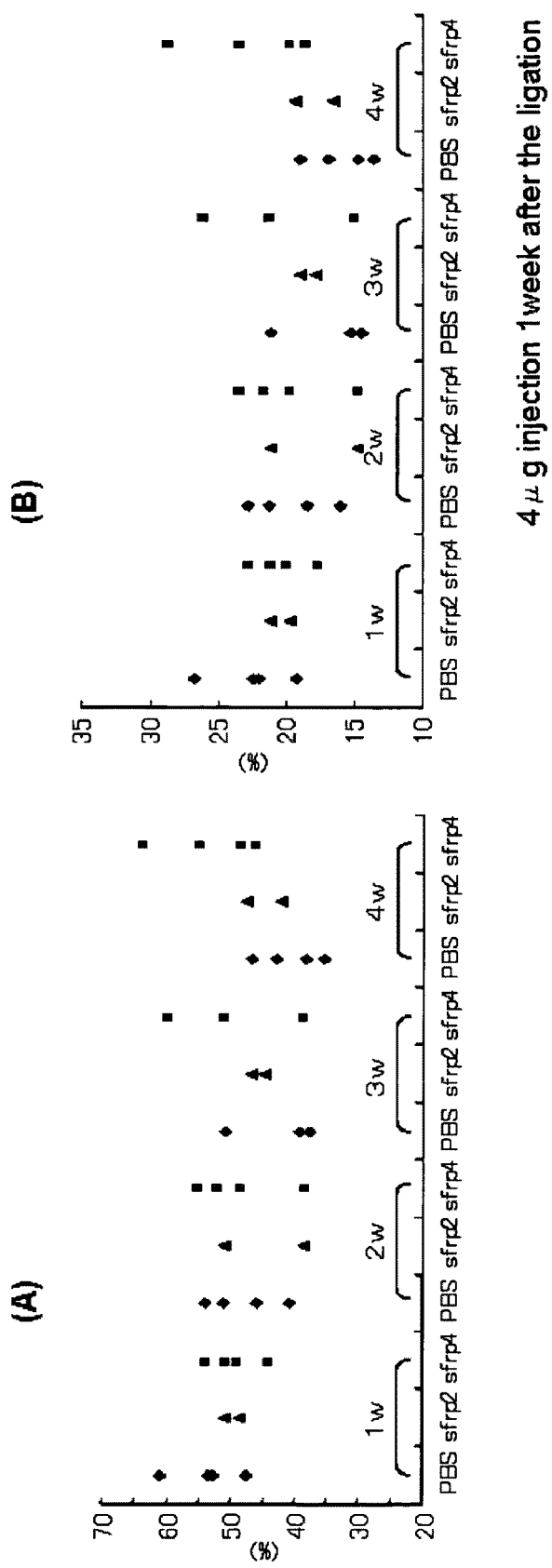
FIG. 7 is a dot plot of echocardiographic measurements of the Ejection fraction (A) and Fractional shortening (B) for intracardiac administration of sfrp2, sfrp4 or PBS to the infarcted hearts of rats obtained in Examples 15 and 16, and Comparative Example 4, respectively.
Figure 8:
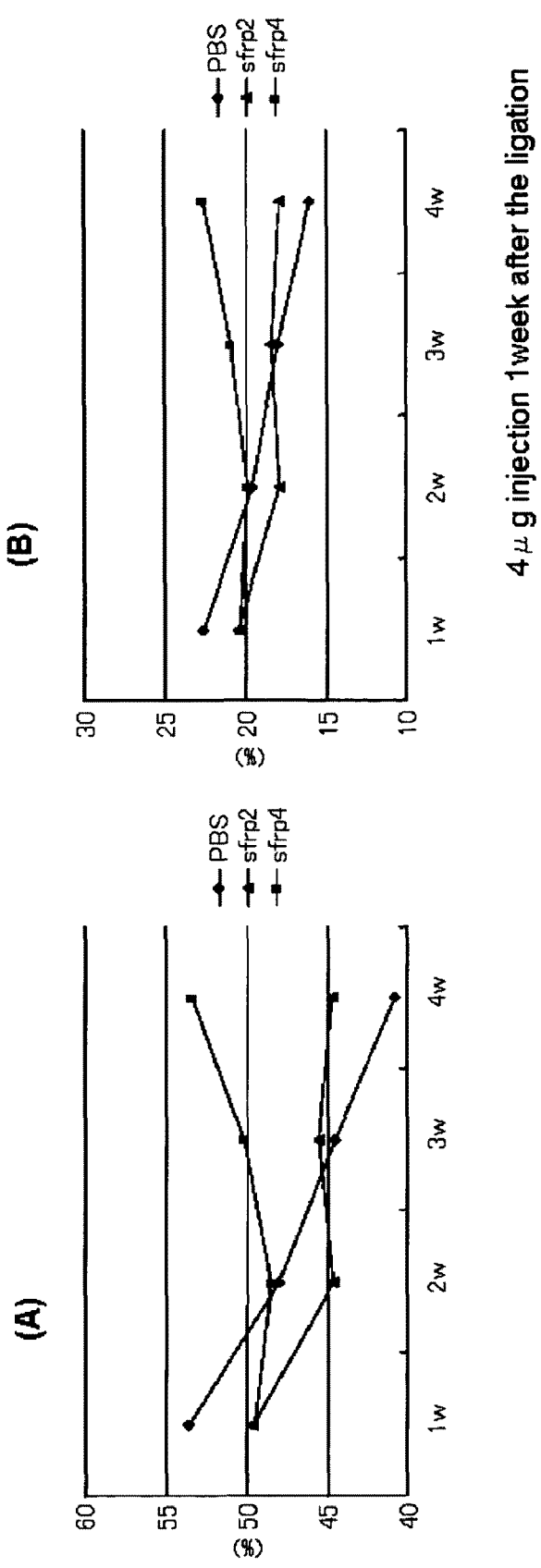
FIG. 8 is a line graph of echocardiographic measurements of the Ejection fraction (A) and Fractional shortening (B) for intracardiac administration of sfrp2, sfrp4 or PBS to the infarcted hearts of rats obtained in Examples 15 and 16, and Comparative Example 4, respectively, which is a graph redrawing FIG. 7.
Figure 9:
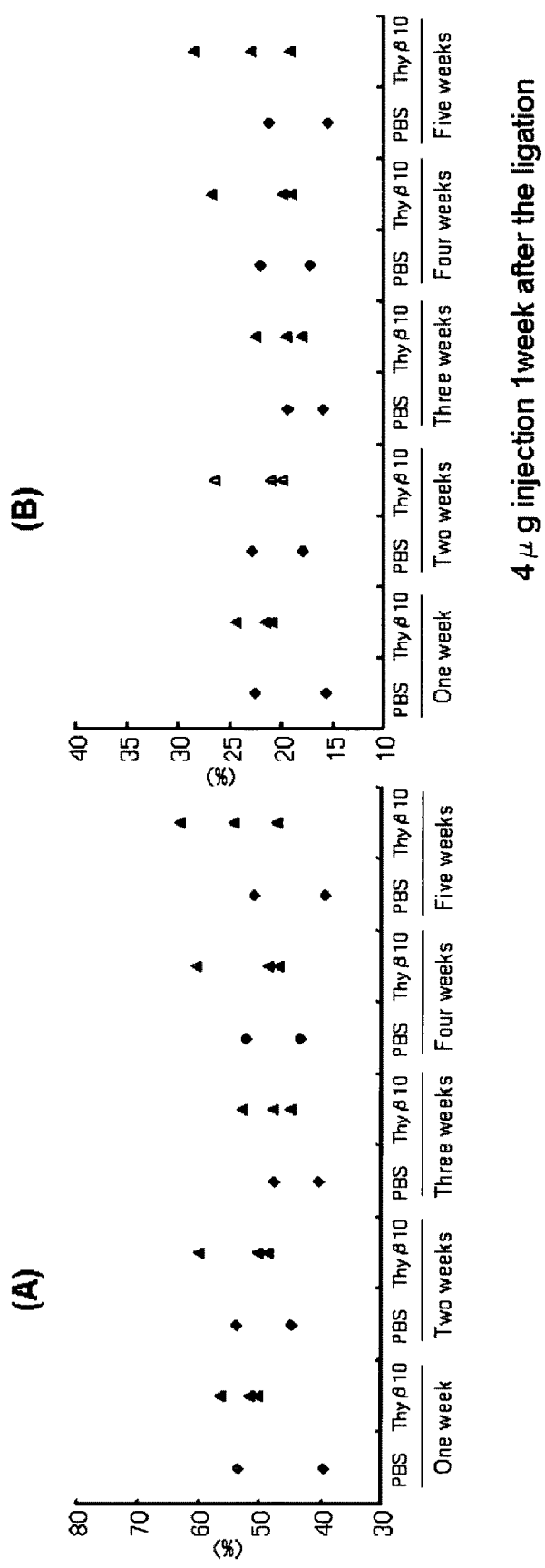
FIG. 9 is a dot plot of echocardiographic measurements of the Ejection fraction (A) and Fractional shortening (B) for intracardiac administration of thymosin β10 or PBS to the infarcted hearts of rats obtained in Examples 17 and those in Comparative Example 5.
Figure 10:
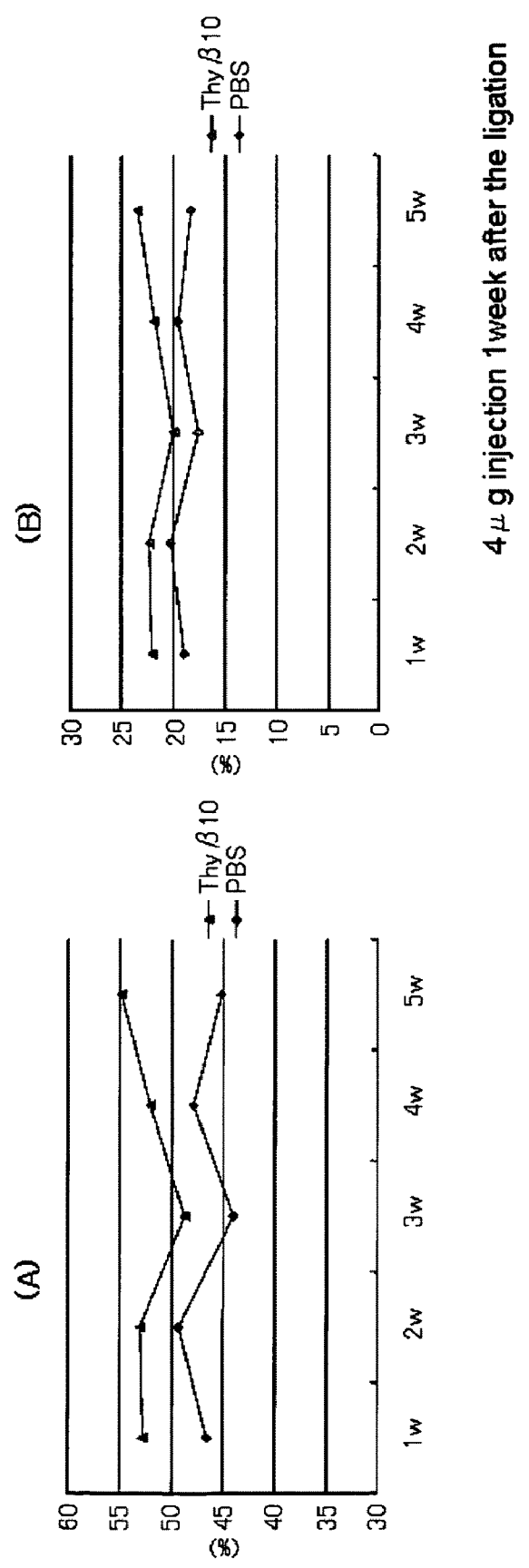
FIG. 10 is a line graph of echocardiographic measurements of the Ejection fraction (A) and Fractional shortening (B) for intracardiac administration of thymosin β10 or PBS to the infarcted hearts of rats obtained in Examples 17 and those in Comparative Example 5, which is a graph redrawing FIG. 9.

Assessment of Cardiaomyocyte Remodeling Shown in FIG. 6

To clarify a cellular basis for the increase of the non-infarcted myocardial area, gel-alone-treated or 25 μg of MDK-treated hearts were removed 6 weeks after the treatment and PAS-stained (data not shown). Cardiomyocytes in the gel-alone-treated group were significantly wider in their diameter (FIG. 6A), longer in their length (FIG. 6B), and larger in their cell size (FIG. 6C), reflecting volume and pressure overloads after the myocardial infarction. In contrast, although cardiomyocytes in the MDK-treated hearts appeared to be slightly larger than those in non-infarcted normal hearts, they were significantly less hypertrophic if compared to those in the gel-treated control hearts. This result was surprising because the MDK-treated hearts showed increased muscle volume compared to the gel-treated hearts and strongly suggested that the number of cardiomyocyte must be greater in the MDK-treated hearts than that in the gel-treated hearts.

In Examples 15 to 17 and Comparative Examples 4 to 5, various amount of SFRP2, SFRP4, and TB10 were injected 1 week after the ligation. LV functions of the treated rats were echocardiographically monitored at 1, 2, 3, 4, and 5 weeks after the cytokine injection in comparison with those treated with PBS. The cardiac function was evaluated with ultrasonic cardiography M2424A SONOS-7500 Rev.D.2 (Philips, Philips Medical System Osaka, Japan) using a 12-MHz annular array transducer under anesthesia with diethyl ether. The hearts were imaged in short-axis 2D views at the level of papillary muscles and LV end-systolic area (LVESA), LV end-diastolic area (LVEDA), LV dimensions at end-systole and end-diastole (LVDs, LVDd) were determined. Ejection fraction (EF) were calculated by Pombo's method as EF (%)={(LVDd$^3$−LVDs$^3$)/LVDd$^3$}×100. Fractional shortening (FS) or FS in percentage was determined by the equation: FS (%)=LVDd−LVDs/LVDd×100.

The EF and FS of the control hearts constantly decreased after the treatment. In contrast, those of the SFRP2, SFRP4 and TB10-treated hearts were increasingly improved and at 4 or 5 weeks significantly better than those of control hearts (FIGS. 7 to 10). The effect of SFRP2 was smaller than that of SFRP4. These results suggest that intracardiac administration of SFRP2, SFRP4 and TB10 functionally improve the damaged myocardium after ischemic heart disease as in the case of MDK (see Examples 12 to 14).

INDUSTRIAL APPLICABILITY

The present invention provides a method of treatment for ischemic heart disease by promoting scar formation without fibrosis derived from host cells, and a drug ischemic myocardial injury used therein having a therapeutic potential such as their angiogenic, anti-apoptotic, and growth-promoting activities.

TABLE 1

Cardiac functions of the infarcted rats after PTN or MDK injection

|  | LVEDA | LVESA | EF | HR | mean BP |
|---|---|---|---|---|---|
| Gel-alone at baseline | 60.4 ± 2.4 | 38.7 ± 2.8 | 47.3 ± 1.6 | 369.5 ± 6.5 | 74.5 ± 3.0 |
| 6 weeks after injection | 73.5 ± 4.0** | 48.2 ± 3.7** | 39.7 ± 1.7** | 357.5 ± 12.5 | 81.9 ± 4.4 |
| MDK 1 μg at baseline | 61.0 ± 2.2 | 39.9 ± 2.5 | 46.8 ± 1.6 | 374.4 ± 6.0 | 74.0 ± 4.3 |
| 6 weeks after injection | 74.6 ± 5.7* | 50.2 ± 5.5* | 35.4 ± 3.0* | 377.0 ± 13.7 | 70.0 ± 6.4 |
| MDK 5 μg at baseline | 56.8 ± 2.2 | 35.6 ± 1.8 | 49.1 ± 2.9 | 361.8 ± 13.0 | 90.8 ± 3.8 |
| 6 weeks after injection | 58.2 ± 3.0 | 35.3 ± 2.7 | 53.8 ± 3.9 | 362.9 ± 11.9 | 77.9 ± 3.4 |
| MDK 25 μg at baseline | 65.4 ± 3.0 | 41.3 ± 2.4 | 48.9 ± 1.1 | 371.2 ± 12.6 | 79.7 ± 3.3 |
| 6 weeks after injection | 66.7 ± 4.4 | 40.9 ± 3.9 | 51.4 ± 2.8 | 355.9 ± 10.5 | 72.3 ± 4.4 |
| PTN 1 μg at baseline | 64.7 ± 1.5 | 43.4 ± 1.7 | 46.4 ± 1.5 | 382.0 ± 12.9 | 79.4 ± 6.1 |
| 6 weeks after injection | 82.7 ± 6.5* | 57.5 ± 8.5 | 36.7 ± 0.9* | 342.0 ± 14.7 | 77.3 ± 6.0 |
| PTN 5 μg at baseline | 65.0 ± 2.1 | 39.6 ± 2.2 | 46.7 ± 2.2 | 368.6 ± 16.1 | 81.0 ± 3.5 |
| 6 weeks after injection | 70.6 ± 4.8 | 43.7 ± 3.8 | 49.8 ± 2.1 | 364.4 ± 9.1 | 77.2 ± 4.5 |
| PTN 25 μg at baseline | 64.2 ± 0.8 | 41.3 ± 1.6 | 47.5 ± 1.7 | 365.5 ± 5.2 | 74.3 ± 3.8 |
| 6 weeks after injection | 76.3 ± 3.5** | 49.2 ± 3.9* | 47.8 ± 2.5 | 350.2 ± 8.2 | 74.6 ± 2.9 |

LVEDA: left ventricular end diastolic area,
LVESA: left ventricular end systolic area,
EF: ejection fraction,
HR: heart rates,
BP: blood pressure.
N = 10 for each group,
*P < 0.05 vs baseline in the same group;
**P < 0.01 vs baseline in the same group.

The invention claimed is:

1. A method of treatment for ischemic heart disease administering a scar formation accelerator containing SFRP4 as an effective ingredient to promote scar formation, and thereby repair a damaged myocardiac tissue.

2. The method according to claim 1, wherein the scar formation accelerator comprises SFRP4 inserted in delivery vehicles.

3. The method according to claim 2, wherein the scar formation accelerator comprises SFRP4 inserted in delivery vehicles supported on and/or anchored to a sheet.

4. The method according to claim 1, wherein the scar formation accelerator comprises a slow-releasing agent.

5. The method according to claim 4, wherein the slow-releasing agent is SFRP4 inserted in delivery vehicles.

6. The method according to claim 4, wherein the SFRP4 inserted in delivery vehicles is SFRP4 encapsulated in gelatin or mixed with collagen.

7. The method according to claim 1, wherein the scar formation accelerator comprises a slow-releasing agent supported on and/or anchored to a sheet.

* * * * *